United States Patent [19]

Jelly

[11] Plant 4,983

[45] Feb. 15, 1983

[54] SEEDLING ROSE NAMED HILSET

[75] Inventor: Robert G. Jelly, Richmond, Ind.

[73] Assignee: E. G. Hill Co., Inc., Richmond, Ind.

[21] Appl. No.: 292,887

[22] Filed: Aug. 14, 1981

[51] Int. Cl.[3] ..... A01H 5/00

[52] U.S. Cl. ..... Plt./26

[58] Field of Search ..... Plt./26

*Primary Examiner*—Robert E. Bagwill

*Attorney, Agent, or Firm*—Chas. W. Rummler

[57] ABSTRACT

A pink floribunda rose intended for greenhouse culture and the production of cut flowers, this new plant being characterized by a free and abundant production of medium large blooms having excellent keeping tendencies and a moderately spicy fragrance in greenhouse. This new rose exhibits a clear light pink color throughout all seasons.

1 Drawing Figure

BACKGROUND OF THE NEW PLANT

This new rose originated as a seedling resulting from my crossing of undisseminated seedlings at Richmond, Ind., in the Fall of 1973 with the object of combining the pink color of its pollen parent and to retain the keeping quality of its seed parent. The first flowers appeared in the Spring of 1974 and extensive testing of the plant through repeated propations by grafting, under my direction, at Richmond, Ind., and by budding at Livermore, Calif., has demonstrated that the distinctive characteristics of the plant hold true from generation to generation and appear to be firmly fixed.

DESCRIPTION OF THE DRAWING

My new rose plant is illustrated by the accompanying photographic drawing which, in full color, shows face views of a newly opened flower and a three day opened flower, buds in three stages of opening, and specimens of foliage and wood, the color rendition of this drawing being as nearly true as is reasonably possible to obtain by conventional photographic procedures.

DESCRIPTION OF THE NEW VARIETY

The following is a detailed description of my new rose plant based upon observation of plants grown in greenhouse at Richmond, Ind., in March of 1981, the color designations being according to The R.H.S. Colour Chart (R.H.S.) published by The Royal Horticultural Society of London, England, the Horticultural Colour Chart by Robert S. Wilson (W), and the Nickerson Color Fan (N).

THE PLANT

Origin: Seedling No. 64-74ps.

Parentage:

*Seed parent.*—Undisseminated seedling No. 9-67ps.

*Pollen parent.*—Undisseminated seedling No. 27-64o.

Classification: Floribunda.

Type: Plant for greenhouse culture to produce cut flowers.

Form: Bush.

Growth: Moderately free and vigorous.

Habit: Upright and much branched.

Canes: Medium in diameter.

Main stems:

*Color.*—Spinach Green 0960/1 (W).

*Thorns.*—Few, of medium length and straight with a short and narrow base. Color: A shade between Grayed Orange 165B and 165A (R.H.S.).

*Prickles and hairs.*—None.

Branches:

*Color.*—Yellow Green 146C (R.H.S.) spotted with 144B (R.H.S.).

*Thorns.*—Few, long, straight and angled downward from a long and narrow base. Color: Red Purple 61B (R.H.S.).

*Prickles and hairs.*—None.

Foliage:

*Quantity.*—Moderately abundant.

*Form of leaves.*—Odd pinnate. Size: Medium to large.

*Leaflets.*—3, 5 and 7 in number. Shape: Ovate with acute apex and round base and simply serrate margins. Aspect: Moderately thick and leathery. Color: Young leaves: Upper surface — Yellow Green 147A (R.H.S.) with venation Grayed Red 182A (R.H.S.) to Orange Group 29C (R.H.S.) near the margins. Under surface — A shade between Lavender Green 000761/1 (W) and 000761 (W). Mature leaves: Upper surface — A shade between Parsley Green 00962 (W) and Yellow Green 147A (R.H.S.) with venation from Grayed Red 178A (R.H.S.) to Orange 29C (R.H.S.) near leaf margins. Under surface — A shade between Lavender Green 00761/1 and 000761 (W).

*Rachis.*—Upper side — Smooth, grooved, prickles small and widely separated, almost smooth. Under side — Almost smooth.

*Stipules.*—Medium in length, moderately narrow, with points of medium length turning out at an angle of less than 45°.

THE BUD

Before calyx breaks:

*Size.*—Medium large.

*Form.*—Long pointed, with conspicuous neck and with foliaceous appendages on the surface of the bud having slender bristle-like foliaceous parts extending beyond the tip of the bud equal to about three-fourths or more of its length.

*Color of calyx.*—A shade between Yellow Green 144C (R.H.S.) at the center to Green 143C (R.H.S.) at the margin, the tip of the foliaceous part being margined by a shade of Red Purple 59C (R.H.S.).

As the calyx breaks:

*Outside petal color.*—Red 36D (R.H.S.).

As the first petal opens:

*Bud size.*—Medium large to large.

*Form.*—Long pointed.

*Color of petal.*—Outside — A shade of Red 36D (R.H.S.) and Pale Pink 2.5R9/3 (N). Inside — From Red Group 39D (R.H.S.) to Moderate Pink 2.5R8/5 (N).

*Character of opening.*—The bud opens well in greenhouse and the color is not affected by hot weather.

*Sepals.*—Permanent and long. Color: Inside — Scheeles Green 860/3 (W) at the point of attachment blended to 860 (W), the main color. Outside — Yellow Green 147C (R.H.S.) at the point of attachment blended to Green 137C (R.H.S.) along the margins.

*Peduncle.*—Long to medium in length, medium diameter, very erect and with smooth bark. Color of bark: A shade between Yellow Green 144A (R.H.S.) and 144B (R.H.S.). Thorns: None. Prickles: From none to numerous in number. Color: Varying from Orange Red 35D (R.H.S.) at the base to Orange Red 35C (R.H.S.) at the tip. Hairs: Few. Color: Red 46A (R.H.S.).

THE FLOWER

Blooming habit: Free and abundant in greenhouse.

Size: Medium large, 3 to 3½ inches in diameter when fully open.

Form: High centered at first with petals being very tightly rolled outward and remaining very tightly rolled outward as the bloom reaches maturity.

Borne: In irregular clusters on moderately strong long to medium length stems but disbudded to one for commercial purposes.

Petalage: Double, with from 19 to 21 petals, arranged regularly.

*Shape of petals.*—Outside and intermediate petals — Round with cuspidate apex. Inside petals — Oval with cuspidate apex.

*Texture.*—Moderately thick and leathery.

*Aspect.*—Inside and outside surfaces — Satiny.

Color:

A. The following is the color description of a newly opened greenhouse rose in the month of March 1981:

Outside Petal

Outside surface: Red 36D (R.H.S.).
Inside surface: A shade of Red 38C and 38D (R.H.S.).

Intermediate Petal

Outside surface: From Red 36D to Red 36C (R.H.S.).
Inside surface: Red 38D (R.H.S.).

Inner Petal

Outside surface: Red 36C (R.H.S.).
Inside surface: Red 38C (R.H.S.).

B. This description was made from a rose that was open for three days in greenhouse in the month of March 1981:

Outside Petal

Outside surface: Red 36D (R.H.S.).
Inside surface: French Rose 520/3 (W).

Intermediate Petal

Outside surface: Red 36D (R.H.S.).
Inside surface: French Rose 520/2 (W).

Inner Petal

Outside surface: Red 36D (R.H.S.).
Inside surface: Dawn Pink 523/2 (W).

C. General color effect of the open bloom:

Newly opened flower: A blend of French Rose 520/3 (W) and Dawn Pink 523/3 (W).
Three days opened flower: Dawn Pink 523/2 (W).

Fragrance: Moderately spicy in greenhouse.

Persistence: The petals hang on and dry.

Lasting quality: 6 to 7 days in March when kept at living room temperature.

REPRODUCTIVE ORGANS

Stamens: Medium in number and regularly arranged about the pistils.

*Filaments.*—Most with anthers and of medium length. Color: Yellow Green 154D (R.H.S.) to Yellow 2D (R.H.S.).

*Anthers.*—Medium in size and all open at once. Color: Slightly brighter than Yellow Orange 22A (R.H.S.).

*Pollen.*—Moderate in amount. Color: A shade of Yellow Orange 23A and 23B (R.H.S.).

Pistils: Few to medium in number.

*Styles.*—Uneven, short to medium in length, moderately thin, and very tightly bunched. Color: Shaded from Yellow 4D (R.H.S.) to Yellow 2D (R.H.S.).

*Stigma.*—Color: Yellow 2D (R.H.S.).

Ovaries: Some protruding from the calyx.

Hips: Medium length, ovoid to pear shaped in form with conspicuous neck and very smooth, thick and fleshy walls.

This new rose variety is particularly distinguished in that it exhibits a clear, light pink color throughout all seasons. This variety is considered to be better than its seed parent in that its color is clear and the bud form is more pointed. Also, this new plant is an improvement on its pollen parent in that it shows increased productivity and is more upright in stature.

I claim:

1. A new and distinct rose plant, substantially as herein shown and described, characterized by its free and abundant production of light pink flowers and its moderately free and vigorous growth habit.

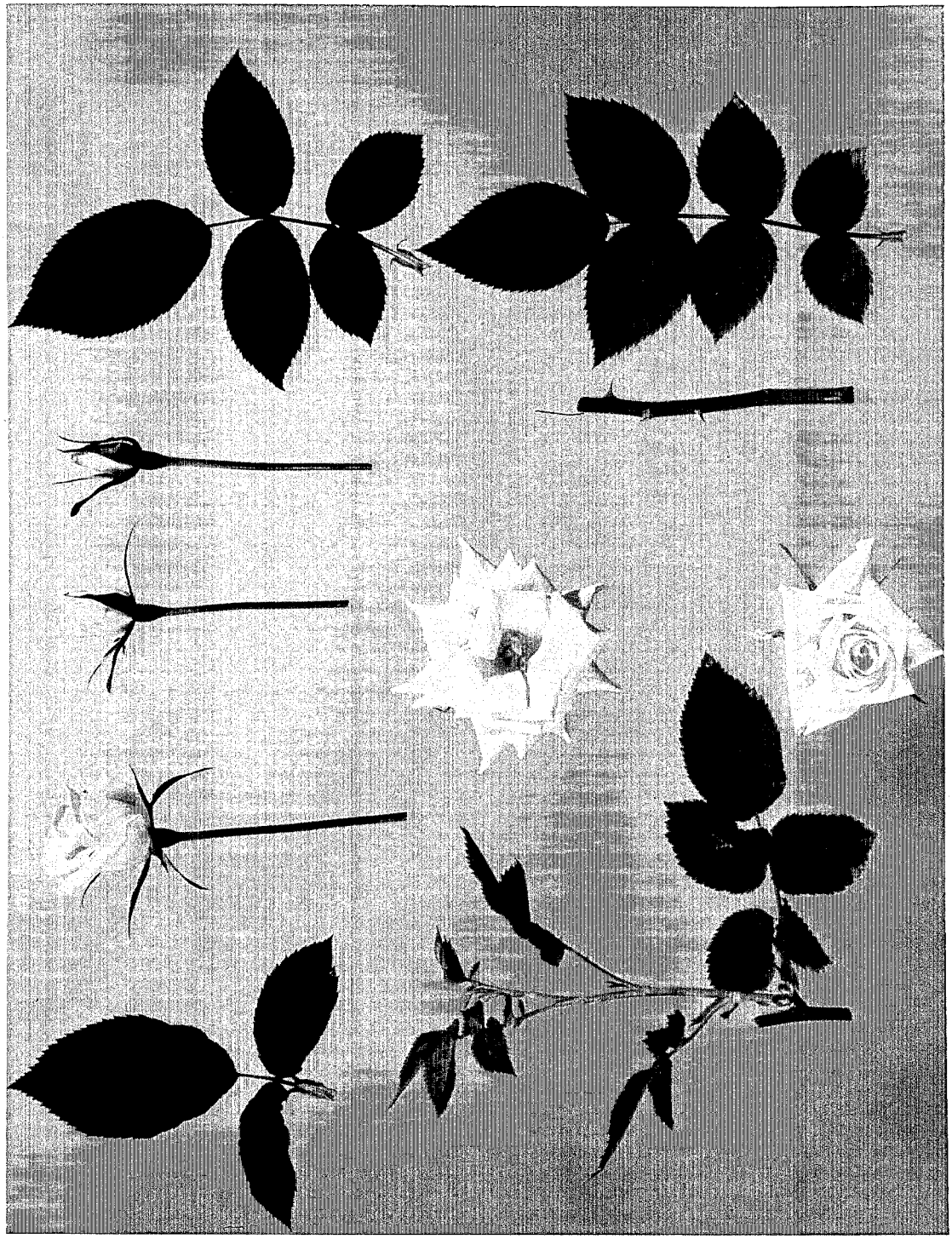

* * * * *